(12) United States Patent
Kawanishi (10) Patent No.: US 6,643,542 B1
(45) Date of Patent: Nov. 4, 2003

(54) HEALTH CONDITION JUDGING/DISPLAYING DEVICE

(75) Inventor: Shozo Kawanishi, Hyogo (JP)

(73) Assignee: Yamato Scale Co., Ltd., Hyogo (JP)

( * ) Notice: Subject to any disclaimer, the term of this patent is extended or adjusted under 35 U.S.C. 154(b) by 71 days.

(21) Appl. No.: 09/830,521

(22) PCT Filed: Aug. 24, 2000

(86) PCT No.: PCT/JP00/05657

§ 371 (c)(1),
(2), (4) Date: Jun. 14, 2001

(87) PCT Pub. No.: WO01/15600

PCT Pub. Date: Mar. 8, 2001

(30) Foreign Application Priority Data

Aug. 27, 1999 (JP) ............................................. 11-241195

(51) Int. Cl.[7] ................................................. A61B 5/05
(52) U.S. Cl. ...................................................... 600/547
(58) Field of Search ................................ 600/547, 372, 600/382; 128/897; 702/19

(56) References Cited

U.S. PATENT DOCUMENTS 5,579,782 A    12/1996  Masuo
5,817,031 A  * 10/1998  Masuo et al. ................ 600/547
6,188,925 B1 *  2/2001  Kawanishi et al. ......... 600/547
6,321,112 B1 * 11/2001  Masuo ......................... 600/547
6,456,873 B1 *  9/2002  Inoue et al. ................. 600/547

FOREIGN PATENT DOCUMENTS

| JP | 07-012635   |   | 1/1995 |
| JP | 09-285455   |   | 11/1997 |
| JP | 11-188016   |   | 7/1999 |
| JP | ep-1092389  | * | 4/2001 |

* cited by examiner

*Primary Examiner*—Mahmoud Gimie
(74) *Attorney, Agent, or Firm*—Marshall, Gerstein & Borun LLP (57) ABSTRACT

A health condition judgment display device comprises an input means with which individual body characteristic information of body of a human subject is input, a measuring means for measuring impedance of body as body measurement information, and weight measuring means for measuring body weight as the body measurement information. The health condition judgment display device is adapted to store body information including the input individual body characteristic information and body measurement information in a data processing portion. By data processing performed by the data processing portion, indices relating to health condition of the human subject are obtained based on the stored body information. The body information and the indices relating health condition are displayed on a display means.

20 Claims, 7 Drawing Sheets

| 31 input/measurement | 32 data processing | 33 indices relating to health condition | 34 degree of various type of body balance |
|---|---|---|---|
| body information · individual body characteristic information · measurement information | for entire body and for each portion · body fat ratio · body fat mass · fat-free mass · body water mass · muscle mass · abdomen visceral fat sectional area | · body mass index (BMI) | 1. body impedance ratio |
| | | · body fat ratio | · [left arm + waist + left leg]/[right arm + waist + right leg] |
| | | · visceral fat mass/subcutaneous fat mass | · left arm/right arm |
| | | · abdomen visceral fat sectional area | · left leg/right leg |
| | | · waist size | · [left arm + waist + right arm]/[left leg + right leg] |
| | | · odds ratio | · [left arm + right arm] / [left leg + right leg] |
| | | · V/S ratio | 2. body water mass ratio |
| | | · W/H ratio | · [left arm + waist + left leg]/[right arm + waist + right leg] |
| | | · F/M ratio | · left arm/right arm |
| | | · body water mass/body weight | · left leg/right leg |
| | | · lower limb water mass/upper limb water mass | · [left arm + waist + right arm]/[left leg + right leg] |
| | | · body fat mass/body water mass | · [left arm + right arm]/[left leg + right leg] |
| | | · body fat ratio/leg muscle mass | 3. muscle mass ratio |
| | | | · [left arm + waist + left leg]/[right arm + waist + right leg] |
| | | | · left arm/right arm |
| | | | · left leg/right leg |
| | | | · [left arm + waist + right arm] /[left leg + right leg] |

Fig. 3

| | | diabetes | | | | | | dehydration | P I H (high blood pressure) | | |
|---|---|---|---|---|---|---|---|---|---|---|---|
| | BMI | abdomen visceral fat sectional area (cm²) | waist size (cm) | odds ratio | V/S ratio or fat sectional area ratio | W/H ratio waist size / hip size | F/M ratio body fat mass / muscle mass | body water mass / body weight | leg (lower limb) water mass / arm (upper limb) water mass | body fat ratio / body water mass | body fat ratio / leg muscle mass |
| | body fat ratio | | | | | | | | | | |
| male | 20~25 | 10~15 | less than 100 | less than 85 | less than 1.0 | less than 0.4 | less than 1.0 | | | | |
| female | 19~24 | 20~25 | less than 100 | less than 90 | less than 1.0 | less than 0.4 | less than 0.8 | | | | |
| | more than reference value: risk of obesity | more than reference value: visceral fat type obesity | more than reference value: upper half body type obesity | more than reference value: high correlation between factor (risk factor) and disease reference: BMI (20.0~24.0) (odds ratio =1.0) | more than reference value: visceral fat type obesity | more than reference value: upper half body type obesity | less than reference value: subcutaneous fat type obesity | less than reference value: lower half body type obesity | | | | obesity

Fig. 4

| human subject NO | BMI | body fat ratio | visceral fat sectional area | waist size | odds ratio | V/S ratio | W/H ratio | F/M ratio | total judgment |
|---|---|---|---|---|---|---|---|---|---|
| 1 | ○ | ○ | × | ○ | ○ | ○ | ○ | ○ | ○ |
| 2 | × | × | ○ | × | ○ | × | × | ○ | × |
| 3 | ○ | × | ○ | ○ | ○ | ○ | ○ | × | △ |
| 4 | × | ○ | × | ○ | ○ | ○ | ○ | ○ | △ |

Fig. 5

| | balance portion | body impedance ratio | body water mass ratio | muscle mass ratio |
|---|---|---|---|---|
| degree of balance between left half of body and right half of body | (left arm + waist + left leg)/(right arm + waist + right leg) | | | |
| | left arm/right arm | | | |
| | left leg/right leg | | | |
| degree of balance between upper half of body and lower half of body | (left arm + waist + right arm) /(left leg + right leg) | | | |

HEALTH CONDITION JUDGING/DISPLAYING DEVICE

TECHNICAL FIELD

The present invention relates to a health condition judgment display device capable of obtaining indices relating to health condition of a human subject.

BACKGROUND ART

As a device which gives indicators or advices associated with physical health, in old days, there was a device adapted to judge function of internal organs of body, function of autonomic nerves and the like, from distribution of potentials in a body surface or skin impedance, based on oriental medicine. In recent years, there is a device adapted to obtain various body information as well as body fat mass based on measurement of body impedance corresponding to body electric impedance and judge the condition of physical health.

Also, there are a device adapted to give indicators used for judgment of diabetes as one of today's typical diseases caused by obesity and a device capable of performing more accurate estimation according to verification using CT section imaging analyzer or the like.

A device which obtains the indicators or the like associated with physical health is disclosed in Japanese Laid-Open Patent Publication No. Sho. 48-37591, in which body impedances of hands and feet between left side of body and right side of body are measured and the existence/non-existence of disease is judged according to the balance of the impedances.

A device disclosed in Japanese Laid-Open Patent Publication No. Hei. 11-188016, is capable of making judgment of health condition from basal metabolism amount obtained from fat-free mass obtained by measuring the body impedance and amount of consumed oxygen, and muscle mass obtained from the fat-free mass or the like.

However, the conventional device which obtains the indicators or the like associated with physical health is merely capable of judgment based on a single specified index relating to body or a few specified indices relating to body that are highly correlative, when such indicators are obtained.

Therefore, in cases where total judgment of disease should be made based on a number of factors, misjudgment or inaccurate judgment is made. In particular, in order to accurately judge the existence/non-existence of disease complicatedly associated with various metabolic disorders, such as diabetes, there is a need for total judgment based on more indices.

Accordingly, an object of the present invention is to provide a health condition judgment display device which is capable of making total judgment of health condition.

Disclosure of the Invention

According to the present invention, there is provided a health condition judgment display device comprising: an input means with which individual body characteristic information of body of a human subject is input; a measuring means for measuring body measurement information obtained by measurement made for the body of the human subject; a data processing portion capable of storing body information including the individual body characteristic information of the body input with the input means and the body measurement information measured by the measuring means and obtaining an index relating to health condition of the body of the human subject by data processing based on the stored body information; and a display means capable of displaying the body information including the individual body characteristic information and the body measurement information and the obtained index relating to health condition, wherein at least two indices relating to health condition are obtained.

According to the health condition judgment display device, since at least two types of indices relating to health condition are obtained based on the input body information, total judgment of the health condition of the human subject can be made.

In the health condition judgment display device, the measuring means includes a body impedance measuring means capable of measuring body impedance of entire body and/or each portion of the body, the body measurement information includes body impedance of each portion of the body and/or the entire body, the individual body characteristic information includes body height, body weight, age, and sex, and the body information includes information of body fat mass, body fat ratio, fat-free mass, body water mass, and muscle mass of each portion of the body and/or the entire body, which are obtained based on the body height, the body weight, the age, the sex, and the body impedance of each portion of the body and/or the entire body. Also, the body information may include information of basal metabolism amount obtained from the amount of consumed oxygen and the muscle mass.

In the health condition judgment display device, the body information may include waist size and hip size. The waist size refers to a circumferential dimension of waist of the human subject and the hip size refers to a circumferential dimension of hip of the human subject.

The body information may include subcutaneous fat thickness, abdomen visceral fat sectional area, abdomen subcutaneous fat sectional area, and thigh muscle sectional area.

The indices relating to health condition may include a ratio of the body fat mass to the muscle mass (F/M ratio) for the entire body and each portion of the body.

The body information includes waist size, hip size, subcutaneous fat thickness, abdomen visceral fat sectional area, abdomen subcutaneous fat sectional area, and thigh muscle sectional area, and the indices relating to health condition may include a body mass index (BMI), a ratio of the waist size to the hip size (W/H ratio), a ratio of the visceral fat to the subcutaneous fat (V/S ratio), a ratio of the body fat mass to the body water mass, a ratio of the body water mass to the body weight, and a ratio of the body fat ratio to leg muscle mass. The indices relating to health condition may further include abdomen visceral fat sectional area, waist size, and odds ratio.

The indices relating to health condition include ratios relating to balance of the body impedance, the body water mass, and the muscle mass, between left half of the body and right half of the body.

The indices relating to health condition include ratios relating to balance of the body impedance, the body water mass, and the muscle mass, between upper half of the body and lower half of the body.

In the health condition judgment display device, information of various types of diseases are stored, and items of the indices relating to health condition as factors of each disease and their associated allowable values are stored for each of the diseases, and a comparing means that compares each of the indices relating to health condition to the allowable value is provided.

Thereby, the risk of developing disease is judged based on the indices relating to health condition and according to the relationship with the disease.

When the health condition judgment device is provided with the comparing means, each of the indices is classified into two or more stages based on comparison made by the comparing means. Thereby, the risk of developing disease associated with the obtained indices relating to health condition can be judged with high accuracy.

Also, a combination of two or more indices is obtained according to the stages of each of the indices relating to health, and total judgment of health condition of the human subject is made according to the combination of the indices. Thereby, total judgment of the risk of developing the disease can be made.

The comparing means compares the indices relating to health condition to the allowable values by weighting according to type of the indices and according to type of disease. Using the correlation with disease according to type of the index relating to health condition, the risk of developing the disease can be judged with higher accuracy.

The display means is adapted to select and display the items of the indices relating to health condition which are associated with each of the diseases and the obtained indices relating to health condition, corresponding to the respective items of the indices, for each of the diseases. Thereby, the relationship between the disease and the indices relating to health condition as factors associated with the disease can be easily known.

In the health condition judgment display device, various types of diseases are stored, items of the indices relating to health condition as factors of each disease and their associated allowable values are stored for each of the diseases, a comparing means that compares each of the indices relating to health condition to the allowable value is provided, and it is judged whether each of the indices relating to health condition is good or bad, according to comparison between each of the indices and the allowable value, the display means is adapted to arrange and display results of good or bad, for the respective judged indices relating to health condition, and the results of good or bad are arranged according to degree of correlation with disease associated with the indices.

When the results of good or bad of the judged indices relating to health condition are arranged, to each of results of good and bad of a first index having correlation with disease, results of good and bad of a second index having correlation lower than that of the first index are connected, the results of good and bad of the first and second indices being hierarchically represented, and an appropriate side corresponding to a judgment result for the human subject is selected and displayed, among the results of good and bad of the first and second indices.

The indices for which judgment results are displayed include BMI, body fat ratio, and abdomen visceral fat sectional area.

The results of good or bad for the respective judged indices relating to health condition can be selected and displayed on the display means for each of the diseases.

The information of various types of diseases stored in the health condition judgment display device may include diabetes, dehydration, and metabolic defect.

In the health condition judgment display device, the measuring means may include a body weight measuring means capable of measuring body weight of the human subject.

BEST MODE FOR CARRYING OUT THE INVENTION

Figure 1:
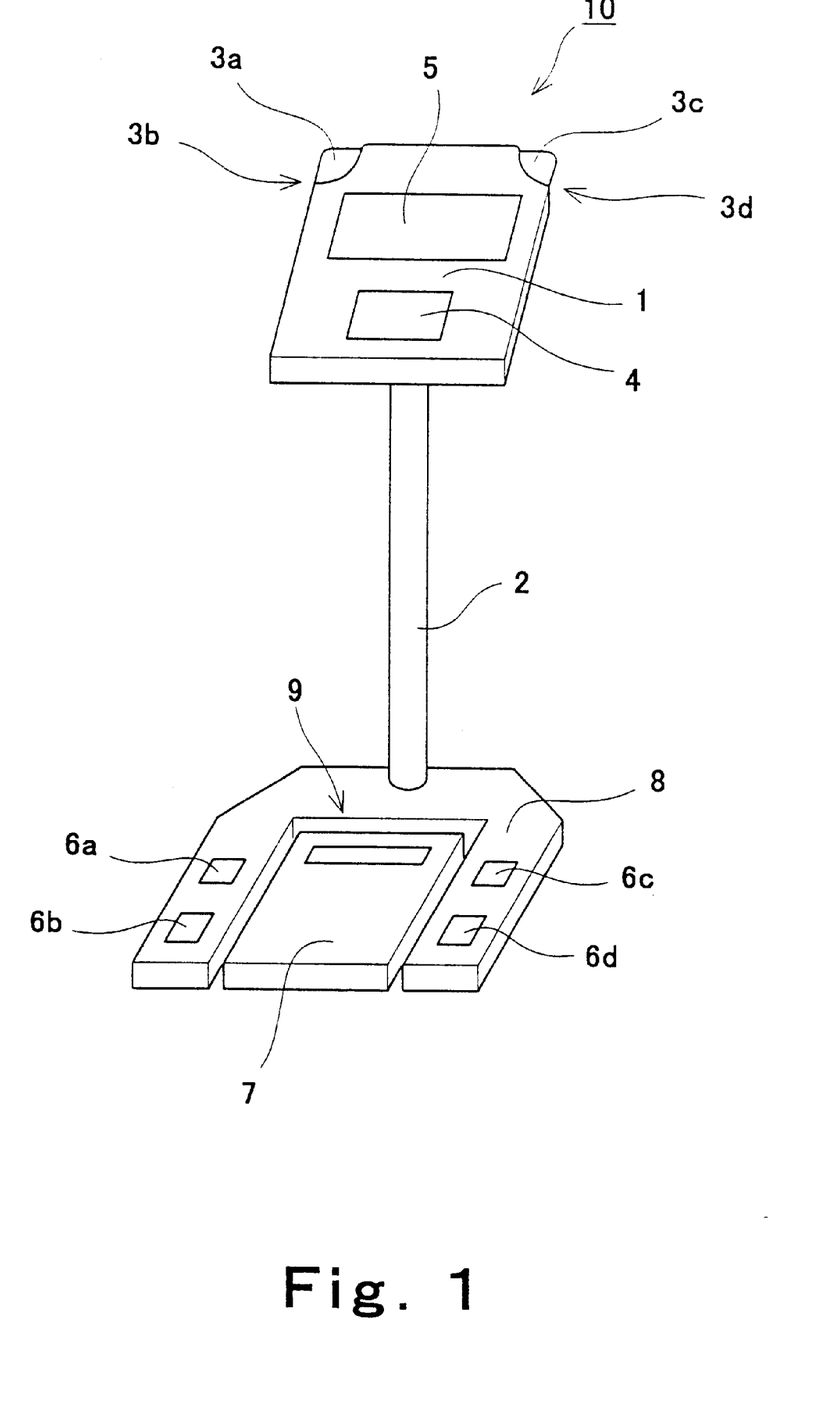
FIG. 1 is a perspective view showing a health condition judgment display device.

An embodiment of the present invention will be described with reference to FIGS. 1 through 7. FIG. 1 is a perspective view showing a health condition judgment display device 10 according to an embodiment of the present invention.

The health condition judgment display device 10 shown in FIG. 1 comprises a base portion 9, a support portion 2 provided on the base portion 9, and an operation panel 1 provided on the support portion 2. The operation panel 1 is provided with a key input portion 4 and a display portion 5.

The key input portion 4 is provided with a number of keys. By operating the keys provided on the key input portion 4, individual body characteristic information of a human subject can be input. The individual body characteristic information input with the key input portion 4 is body height, age, sex, hip size, waist size, and the like.

The display portion 5 is adapted to display the individual body characteristic information, body measurement information such as body impedance mentioned later, body information including these information, and various indices relating to health condition which are obtained based on these information. These information or the like on the display portion 5 can be selectively displayed as necessary.

An electrode 3a is provided at a left end of a tip end portion of a front surface of the operation panel 1 and an electrode 3c is provided at a right end of the tip end portion. An electrode 3b is provided on a portion of a rear surface of the operation panel 1 which substantially corresponds to the portion where the electrode 3a is provided and an electrode 3d is provided on a portion of the rear face which substantially corresponds to the portion where the electrode 3c is provided.

These electrodes 3a, 3b, 3c, 3d serve to measure internal body impedance with both hands as body end portions and constitute a measuring means for measuring the body impedance as the body measurement information.

The electrodes 3a, 3b, 3c, 3d can be used as a pair of current path forming electrodes used for making internal body conduct current to form a current path and a pair of voltage measuring electrodes for measuring a potential difference between two points in the current path.

The electrodes 3a, 3b, 3c, 3d are connected to a body impedance measuring portion 11 provided inside of the health condition judgment display device 10 and the body impedance is measured through these electrodes. The body impedance measuring portion 11 comprises an impedance measuring means having a current supply source, an electrometer, and the like, which are well-known as means for measurement of body fat.

When the impedance of body is measured, two fingers of left hand of the human subject are respectively brought into contact with the electrodes 3a, 3b at the left end and two fingers of right hand of the human subject are respectively brought into contact with the electrodes 3c, 3d at the right end, for measuring the impedance of body.

The base portion 9 connected to the operation panel 1 through the support portion 2 is provided with a weight measuring portion 7 and an electrode sustaining portion 8 formed as separate portions. The weight measuring portion 7 is constituted by a well-known weighing machine. By mounting the human subject's feet on the weight measuring portion, weight of the human subject is measured. The weight measuring portion 7 corresponds to a weight measuring means for measuring weight data as the body measurement information. The weight data measured by the weight measuring portion 7 can be displayed on the display portion 5.

The electrode sustaining portion 8 is provided with four electrodes 6a, 6b, 6c, 6d. The electrodes 6a, 6b are provided on a left side of the electrode sustaining portion 8 and the electrodes 6c, 6d are provided on a right side of the electrode sustaining portion 8.

These electrodes 6a, 6b, 6c, 6d serve to measure internal body impedance with both feet as body end portions and can be used as a pair of current path forming electrodes used for making a portion of the internal body for which impedance is to be detected, conduct current, to form a current path and a pair of voltage measuring electrodes for measuring a potential difference between two points in the current path. The human subject mounts his/her feet on the electrode sustaining portion 8 and makes his/her left sole come into contact with the electrodes 6a, 6b, and make his/her right sole come into contact with the electrodes 6c, 6d, thereby measuring the impedance.

The electrodes 6a, 6b, 6c, 6d are connected to the body impedance measuring portion 11 provided inside of the health condition judgment display device 10 and are adapted to measure the body impedance through these electrodes.

In the health condition judgment display device 10, when measuring the body impedance, the electrodes 3a, 3b, 3c, 3d for hands and the electrodes for feet are suitably selected and used as the current path forming electrodes and the voltage measuring electrodes, as mentioned later. Thereby, impedance of each portion of body as well as impedance of the entire body can be measured. Also, data processing based on the measured impedance can obtain the impedance of each portion.

A multi-frequency current is used as the current output through the electrodes as the current path forming electrodes and various-frequency currents to be conducted can vary according to internal portions of the body for which the impedance is to be measured.

Thus, the health condition judgment display device 10 is capable of measuring the body impedance of each of left arm, right arm, internal portion of waist, left leg, and right leg of body.

As a measuring means for measuring body measurement information, a C/T scan device (not shown in FIG. 1) may be connected to the health condition judgment display device 10. The C/T scan device may be used to image a section of abdomen of the human subject, for measurement of a sectional area of a visceral organ of abdomen and a sectional area of subcutaneous fat of abdomen, which are to be input to the health condition judgment display device 10.

As a measuring means for measuring the body measurement information, a subcutaneous fat meter (not shown in FIG. 1 and generally referred to as "caliper") may be connected. Subcutaneous fat thickness measured by using the caliper may be input to the health condition judgment display device 10.

The use of this subcutaneous fat thickness data complements the data processing relating to information of the body fat obtained based on the body impedance and improves accuracy in information pertaining to the body fat to be measured.

An automatic measuring device for measuring waist size (waist circumference) or hip size (hip circumference) of the human subject may be connected to the health condition judgment display device 10 and the waist size or the hip size measured by the automatic measuring device may be input to the display device 10. Alternatively, the waist size or the hip size may be measured by using a tape measure or the like and so measured values may be input as the individual body characteristic information by operation of a key of the key input portion 4 and used as the body information mentioned later.

Figure 2:
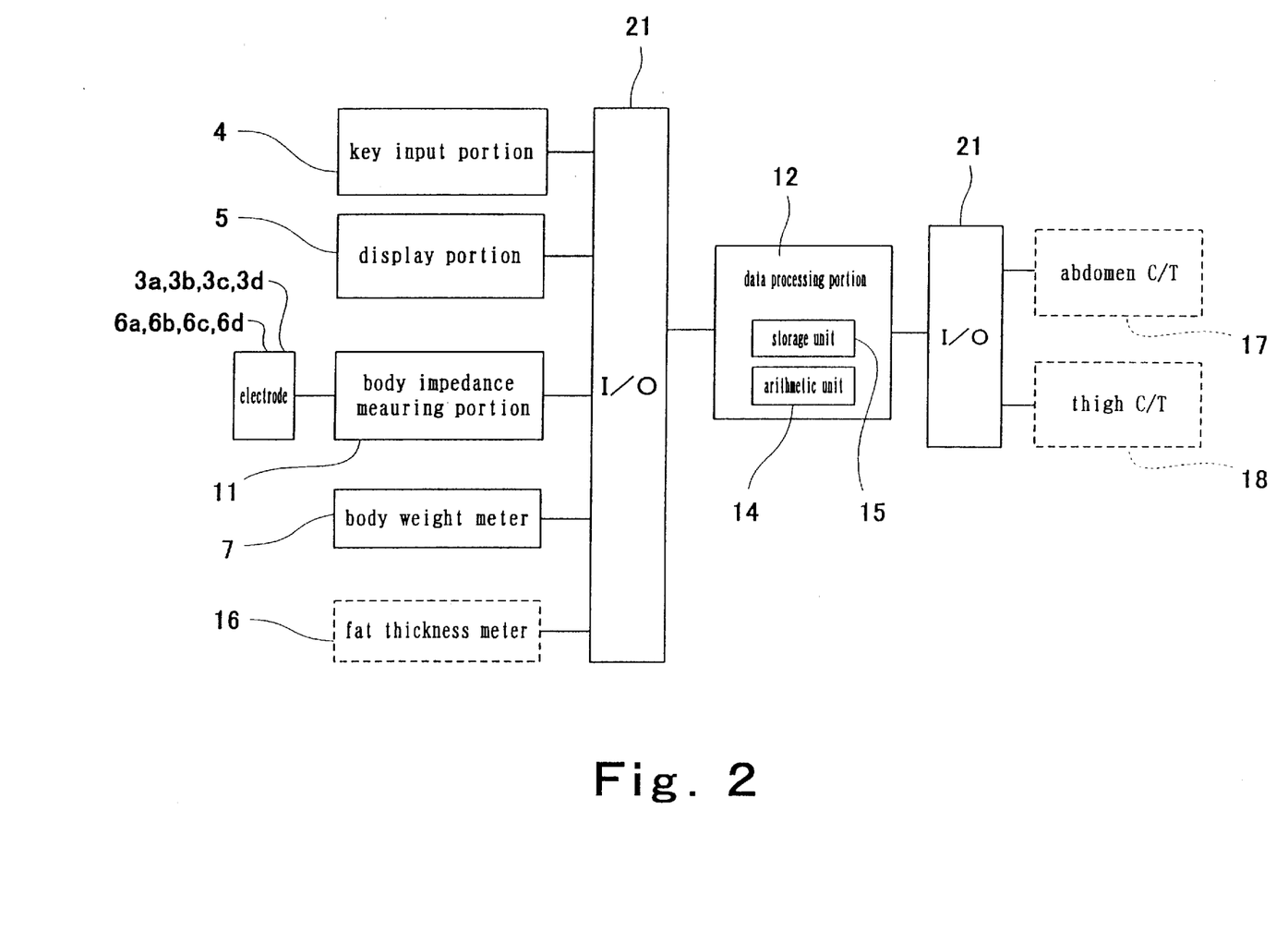
FIG. 2 is a block diagram showing data processing of the heath condition judgment display device.

Subsequently, with reference to FIG. 2, blocks of the data processing of the health condition judgment display device 10 will be described. The individual body characteristic information input by operating the key input portion 4, is input to a data processing portion 12 through an input/output (I/O) portion 21.

The measured-data of the body impedance as the body measurement information which has been measured through the electrodes 3a, 6a, and the like, is input to the data processing portion 12 through the input/output (I/O) portion 21. Selective switching between the current path forming electrodes and the voltage measuring electrodes, corresponding to the eight electrodes 3a, 6a, . . . in measurement of the body impedance, can be performed by operation of the data processing portion 12. Thereby, the current path can be formed in a required portion of the body and a path through which the impedance is detected can be formed, allowing the impedance of each portion of the body to be measured.

The weight data measured by the weight measuring portion 7 is input to the data processing portion 12 through the input/output (I/O) portion 21. When measuring means such as a fat thickness meter 16 for measuring the subcutaneous fat thickness, an abdomen C/T 17 for abdomen measurement, and a thigh C/T 18 for thigh measurement are connected, body measurement information measured by these measuring means is also input to the data processing portion 12 through the input/output (I/O) portion 21.

The data processing portion 12 comprises an arithmetic unit 14 and a storage unit 15. The various individual body characteristic information and body measurement information input to the data processing portion 12 are stored in the storage unit 15. These input data is also stored as the body information. Well-known arithmetic expressions or coefficients used for obtaining indices relating to health condition from the stored body information are also stored in the storage unit 15. The arithmetic unit 14 performs arithmetic operation for obtaining various indices relating to health condition from the body information stored in the storage unit 15.

As described above, the individual body characteristic information, the body measurement information, the body information, and the indices relating to health condition are displayed on the display portion 5. The contents to be displayed are sent from the data input portion 4, the body impedance measuring portion 11, and the data processing portion 12, through the input/output (I/O) portion 21, arid to the display portion 5.

Subsequently, examples of obtained items stored in the storage unit 15 as a result of the input/output operation and the data processing performed by the health condition judgment display device 10, will be described.

Figure 3:
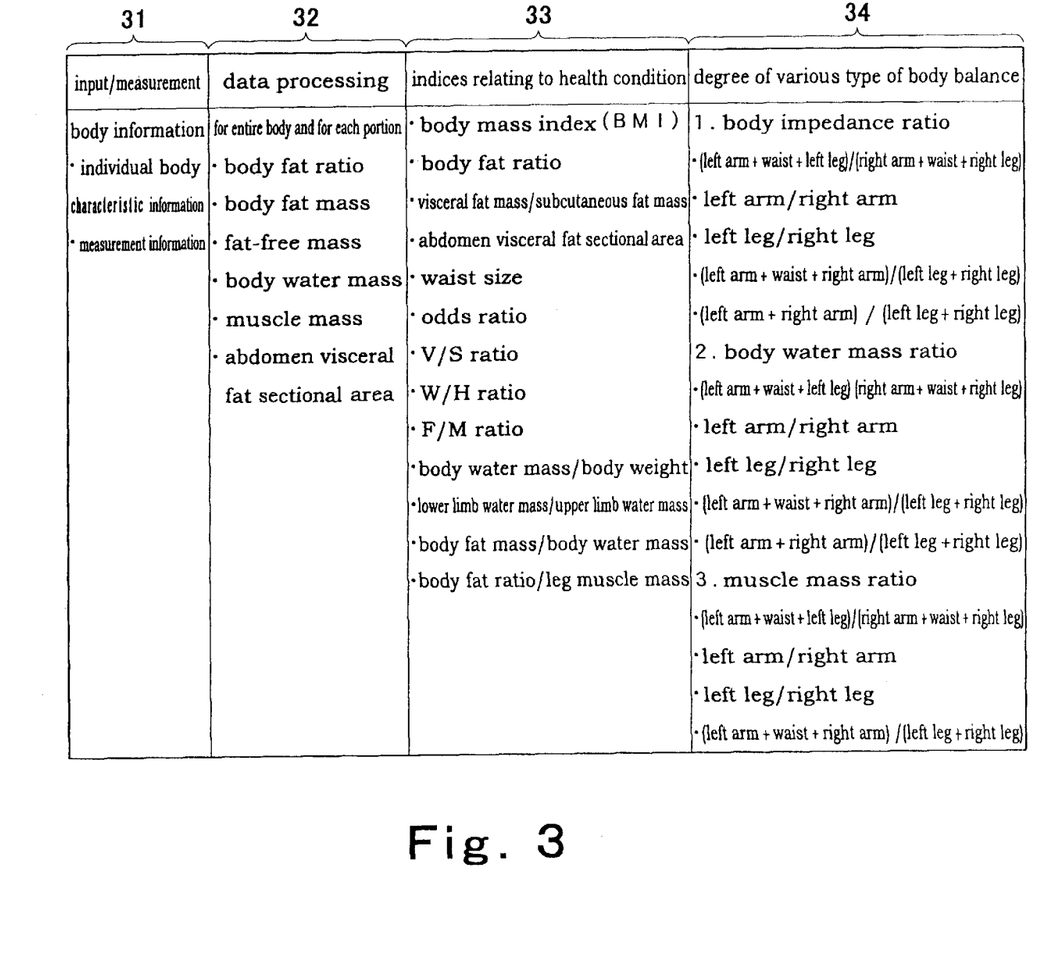
FIG. 3 is a view showing contents stored in a first storage table.

FIG. 3 shows contents of the example of one set of the associated obtained items stored in the first storage table. As can be seen from FIG. 3, the individual body characteristic information input by operation of the key input portion 4, the body measurement information such as the body impedance input through the body impedance measuring portion 11, and the body information composed of these information are stored in a first area 31.

Data obtained by data processing based on the information stored in the first area 31 is stored in a second area 32 in the first storage table. The indices relating to health condition are stored in a third area 33 of the first storage table. In some cases, the data stored in the second area 32 is stored in the third area as the indices relating to health condition. Degrees of balance indicating balance between portions of body as one of the indices relating to health condition are stored in a fourth area 34 of the first storage table.

The various types of data stored in the first storage table will be explained below.

Body fat ratio, body fat mass, and body water mass are obtained by data processing based on the body impedance as the body information. By auxiliarily using subcutaneous fat thickness data as described above, precision in data processing can be improved.

When obtaining the body water mass, the multi-frequency current is used to measure the body impedance. Thereby, mass of liquid outside of cells and the body water mass are obtained, and from difference between these, the mass of liquid in the cells is obtained. Then, the fat-free mass is obtained from the body water mass or the like. Further, the muscle mass is obtained from the fat-free mass, bone mass, and lipid mass. Moreover, basal metabolism amount is obtained from the fat-free mass and the amount of consumed oxygen.

A body mass index is obtained as a ratio of body weight to body height squared (body weight/(body height×body height)). Since the body mass index lowly correlates with body height and highly correlates with fat mass, it is called BMI and is an international index used for judging whether the human subject is obese/underweight. From this value, a standard weight ratio is obtained and obesity is classified into five stages as: less than −20%: Extreme Underweight, −20% to −10%: Underweight, −10% to +10%: Normal, +10% to +20%: Overweight, and more than +20%: Extreme Obesity). These obesity classes serve as an index for judgment of diabetes highly correlative with obesity.

The body fat ratio can be used as the index used for accurately judging whether or not the human subject is obese. The body fat ratio can be obtained from body impedance of the entire body, and the individual body characteristic information such as body height, age, body weight, sex and the like. From the body fat ratio, the obesity is classified into four stages for male and female (Male/0 to 10%: Underweight, 10% to 15%: Normal, 15% to 20%: Overweight, 20% or more: Extreme overweight, Female/0 to 20%: Underweight, 20% to 25%: Normal, 25% to 30%: Overweight, 30% or more: Extreme overweight). Like the BMI, the body fat ratio can be used for judgment of diabetes as the index accurately indicating the obesity class. It should be noted that the body fat ratio refers to an internal fat ratio of the entire body and the internal body fat ratio refers to a fat ratio of each portion of the body and the entire body.

An odds ratio is an index indicating how possible that a person having a risk factor exceeds an outcome as compared to a person which has no risk factor, that is, how many times the odds is. To evaluate correlation between the BMI value and diabetes, high blood pressure, hyperlipemia, and various types of lipid metabolism disorders corresponding to main risk factors of circulatory diseases, data of the odds ratio obtained based on BMI data of not less than 20.0 and less than 24.0 (median=22.0) among BMI data in a group model is referred to (for example, see document published by Japanese Obesity Institution). Thereby, correlation between the BMI and the incidence of diabetes, high blood pressure, hyperlipemia, and various types of lipid metabolism disorders can be obtained. In this way, the odds ratio can be used as the index indicating degree of correlation between factors and disease.

A ratio of visceral fat mass (V) to subcutaneous fat mass (S) (V/S ratio), (or visceral fat mass and subcutaneous fat mass) can be used as the index, from which spots of body at which body fat is deposited, i.e., distribution of body fat, is known. Therefore, the V/S ratio can be used as the reference to correctly know health condition. As the V/S ratio, a ratio of the visceral fat sectional area to the subcutaneous fat sectional area may be obtained.

Obesity in which much visceral fat is deposited is named visceral-type obesity (V/S>0.4: visceral fat deposition type obesity, V/S<0.4: subcutaneous fat deposition type obesity), and it is proved that this obesity highly correlates with disease such as diabetes and insulin resistance. According to type of obesity, it is judged whether or not the human subject is likely to develop diabetes, hyperlipemia, and lipid metabolism disorder.

Therefore, the V/S ratio can be used as an important index from which accurate judgment of these diseases is made. The visceral fat and subcutaneous fat as basic data from which the V/S ratio is obtained, can be obtained based on measurement of the body impedance, and can be also obtained from measurement of a sectional area of each fat by using a C/T device. Further, a visceral fat sectional area of abdomen can be estimated from waist size or a ratio of waist size to hip size. The subcutaneous fat can be easily obtained by directly measuring its thickness by using the caliper.

A ratio of waist size (W) to hip size (H) (W/H ratio) can be also used as the index based on the spots at which the fat is deposited. Obesity with high W/H ratio is named upper half body obesity and obesity with low W/H ratio is named lower half body obesity. A person of the upper half body obesity is considered to have complication such as glucose metabolism disorder and lipid metabolism disorder. When a man has the W/H ratio greater than 1.0 and a woman has the W/H ratio greater than 0.8, probability that he/she has various types of metabolic disease is considered to be high.

From a ratio (F/M ratio) of internal fat mass (F) to muscle mass (M), the followings are known. A muscle is an organ that has large energy consumption and large metabolism amount. In particular, the muscle takes in glucose by action of insulin as hormone and therefore plays an important role in metabolism of glucose. With regard to effects of insulin, it is known that the greater the fat mass is, the less effectively insulin works and the more likely diabetes or the like is to develop. Likewise, it is known that the less the muscle mass is, the less effectively insulin works. It is therefore known that reducing of the fat mass and keeping or increasing of the muscle mass are effective in kinesiology and, active action of muscle increases sensitivity of insulin, causing insulin to work effectively.

It is considered that leg muscle mass is an index as a result of appropriate kinesiology such as walking. By comparison with the fat mass (internal fat mass/leg muscle mass, internal body fat ratio/leg muscle mass), the leg muscle mass can be used for accurate judgment. In recent years, in kinesiology for physical and mental recovery for a patient after a cardiac disease such a cardiac infarction, ergometer is used to measure lower limb muscle mass correlative with recovery, for estimation and evaluation of degree of improvement of exercise-resistance ability. In this case, the thigh CT imaging device is used to measure a sectional area of thigh muscle as the muscle mass, for estimation and evaluation of the degree of improvement of the exercise-resistance ability.

The body water mass can be used as the index indicating whether or not the body water mass of the human subject is in a proper range, in comparison with his/her body weight. In particular, the body water mass is advantageous when used as the index of dehydration of an old person who often has complications. Further, water distribution or body impedance distribution of body (associated with interior/exterior of cells, upper half of body, or lower half of body) is obtained, and is monitored with an elapse of time so that metabolic ability of body can be estimated and improvement of the exercise-resistance ability in kinesiology can be evaluated. These distribution can be used for grasping the state of diseases such as heart disease and kidney disease, causing various water distribution abnormality (for example, monitor in artificial dialysis, monitor of a patient after disease, and so forth) and treatment of the disease.

Lower limb water mass/upper limb water mass is used as an index for high blood pressure (PIH) triggered by pregnancy. Using the lower limb water mass/upper limb water mass, a characteristic change of the PIH in which water is deposited in leg can be measured. The lower limb water mass/upper limb water mass can be obtained by measuring the impedance of leg (lower limb) and the impedance of arm (upper limb) and dividing the impedance of leg (lower limb) by the impedance of arm (upper limb).

Also, a ratio between conflicting measured values, for example, body water mass/body fat mass, can be used as an index.

Using the degree of balance, balance between left side of the body and right side of the body and balance between upper side of the body and lower side of the body can be evaluated, with regard to the body impedance, the body water mass, and the muscle mass of body. This degree of balance can be used for judgment of health condition of body. In particular, with regard to evaluation based on the balance associated with the muscle mass, effects of exercise, training, and the like can be evaluated for each portion of body and for entire body, in terms of health and sports medicine. Also, in terms of beauty, balance of the muscle mass can be compared to a target or ideal value, in addition to the conventional body type judgment.

With regard to the indices of degree of balance in the fourth area 34, "left arm" refers to a portion from a base of left arm to a tip end of left hand and "waist" refers to the entire internal waist of body in the vertical direction. For example, (left arm+waist+left leg) represents a sum of indices of left arm, waist, and left leg.

Figure 4:
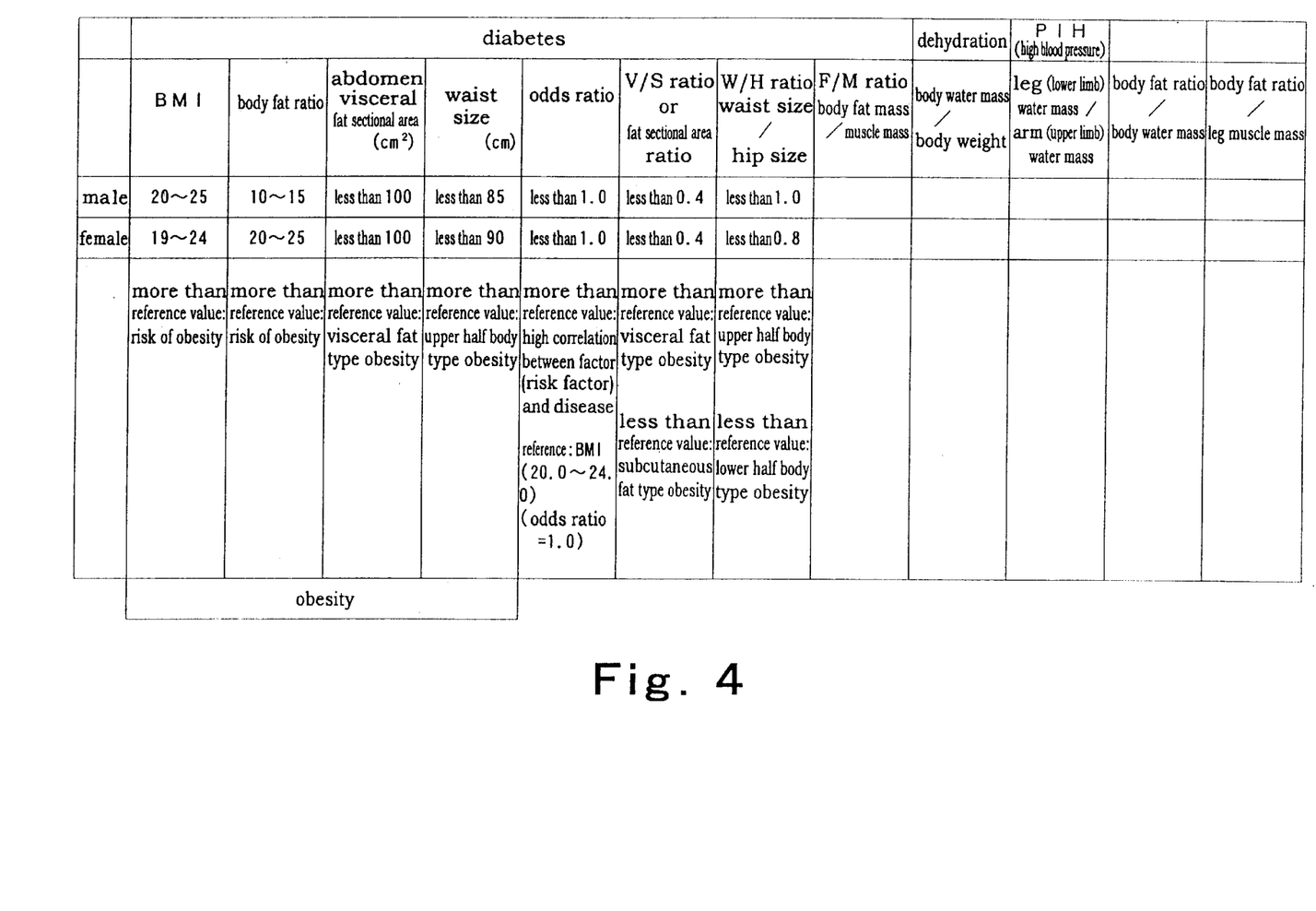
FIG. 4 is a view showing contents stored in a second storage table.

FIG. 4 shows contents of the second storage table as an example of a table stored in the storage unit 15. The second storage table contains allowable values for respective indices relating to health condition as the factors associated with disease, for each disease. The second storage table contains known data and is stored in the storage unit 15.

As shown in FIG. 4, BMI, body fat ratio, abdomen visceral fat sectional area, and waist size as the contents of the second storage table, are associated as factors of diabetes and factors of obesity. It is known that the BMI, the abdomen visceral fat sectional area, and the waist size highly correlates with obesity. Based on these indices, judgment of obesity, i.e., a cause of various types of adult disease, is made.

Figure 5:
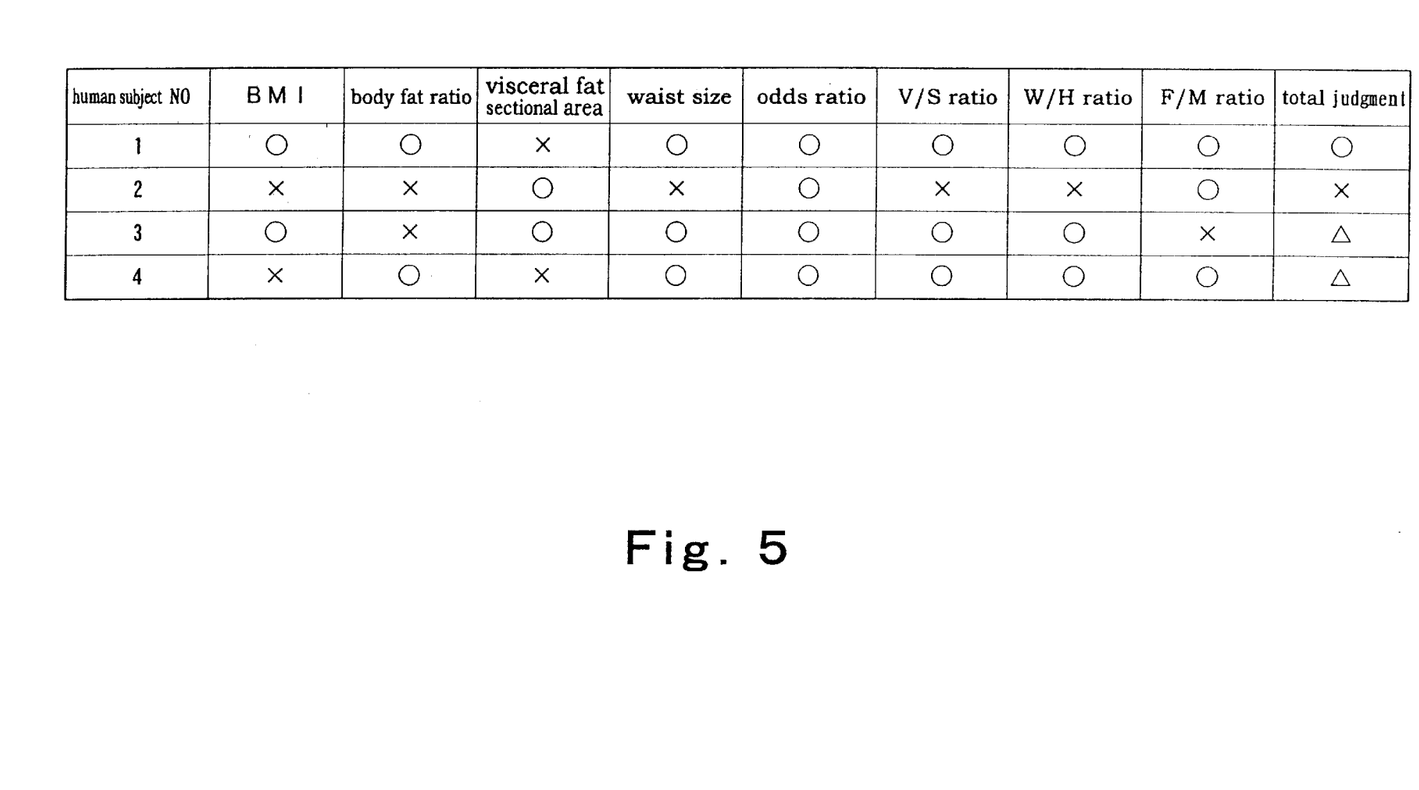
FIG. 5 is a view showing contents stored in a third storage table.

FIG. 5 shows contents of the third table as an example of the table stored in the storage unit 15. The third storage table contains results of comparison made between the indices relating to health condition and the allowable values stored in the second table, with regard to diabetes as one of diseases for each human subject. Total judgment of whether each human subject is at a risk of developing diabetes is stored in a right end area.

In FIG. 5, for each index relating to health condition, when it is less than the allowable value, evaluation is ○ and when it is greater than the allowable value, evaluation is X. In the example shown in FIG. 5, based on the total number of ○ or X as results of the respective indices, total evaluation ○ or X is decided. In the total judgment, evaluation is A, when care should be taken although the evaluation is ○ nor X.

Based on the contents shown in FIGS. 4, 5, judgment of the index such as the obtained BMI is made according to the relationship with disease such as diabetes, and the risk of developing diabetes and the like is determined. As shown in FIG. 5, total judgment of the risk of developing diabetes is objectively made, based on the obtained several indices.

Figure 6:
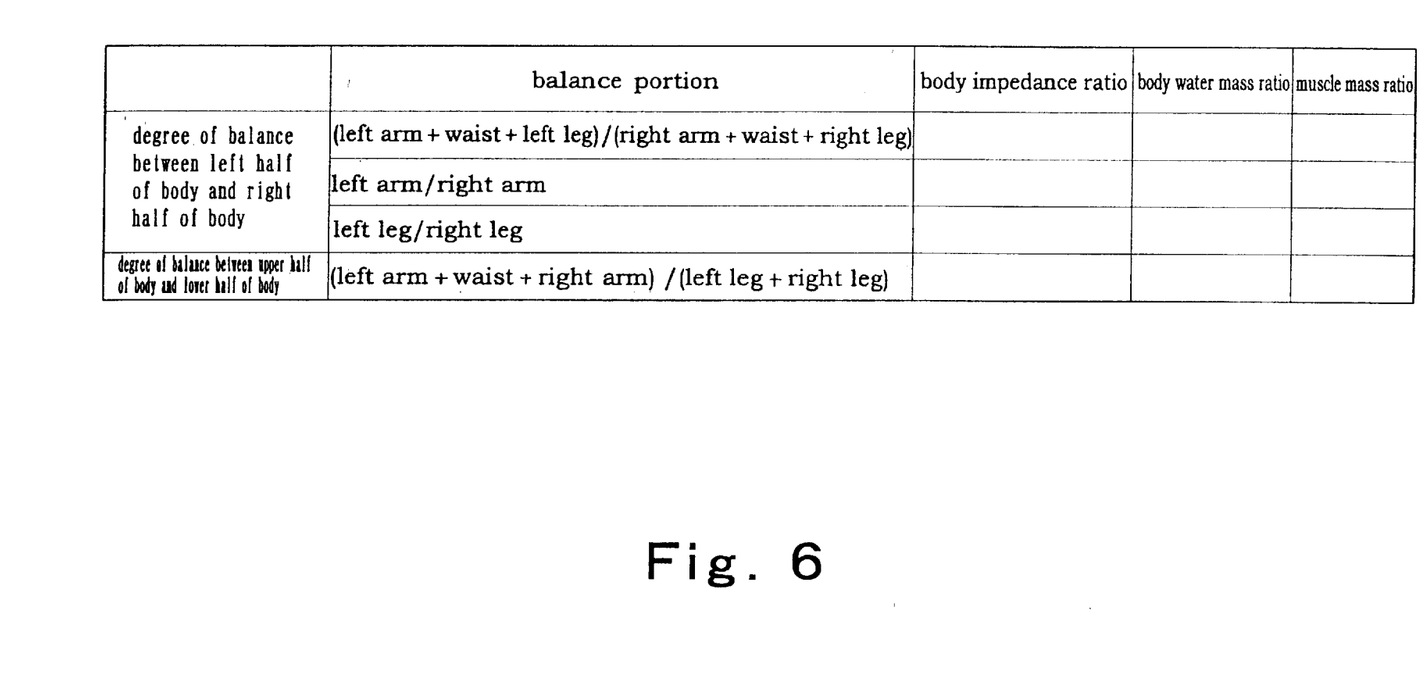
FIG. 6 is a view showing contents stored in a fourth storage table.

FIG. 6 shows contents stored in the fourth storage table as an example of the table stored in the storage unit 15. In the fourth storage table, the various types of degrees of balance stored in the fourth area 34 of the first storage table are arranged for each body information and stored. According to the contents shown in FIG. 6, balance between portions of the body, relating to various indices, can be easily known.

Based on judgment of the respective indices stored in the third storage table shown in FIG. 5, respective indices as factors of the disease and judgment results of the respective indices can be displayed on a display portion 5. In displaying these on the display portion 5, the respective indices can be arranged according to degree of correlation between the indices and disease.

Figure 7:
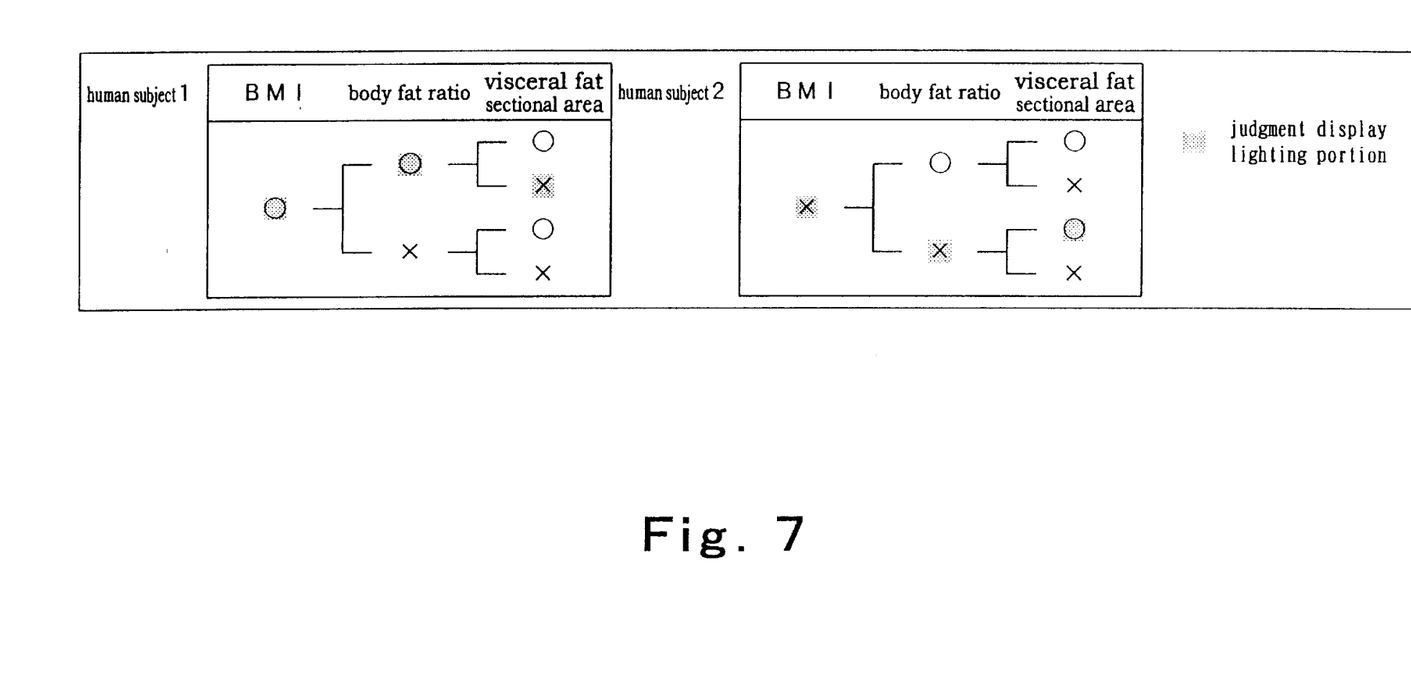
FIG. 7 is a view showing an example of judgment results of respective indices hierarchically displayed.

FIG. 7 shows an example in which the respective indices as factors of disease and judgment results of the respective indices are displayed on the display portion 5. In the example shown in FIG. 7, results for human subjects 1, 2 are displayed. In the example shown in FIG. 7, the respective indices are arranged according to degree of correlation with disease and displayed. As displayed, "BMI" has the highest correlation with disease, "body fat ratio" has the second highest correlation, and "visceral fat sectional area" has the lowest correlation.

As shown in FIG. 7, judgment results of the respective indices are hierarchically branched. For example, for the human subject 1, the followings are shown: the result of BMI in a layer is good (○), results of the body fat ratio in a layer lower than the layer of the BMI are good(○) and bad (X), in a layer lower than the layer in which the result of the body fat ratio is good (○), results of the visceral fat sectional area are good (○) and bad (X), and in a layer lower than the layer in which the result of the body fat ratio is bad (X), results of the visceral fat sectional area are good (○) and bad (X).

For each of the indices, good/bad is selected and displayed by lighting an appropriate side as the result of judgment. In case of the human subject 1, the results of judgment of the BMI and the body fat ratio are good (○), whereas the result of judgment of the visceral fat sectional area is bad (X).

By displaying the results as shown in FIG. 7, different indices associated with disease are associatively branched and displayed on the same screen. Thereby, total judgment becomes possible and relevance of judgment among the respective indices is checked.

For example, in a case where when it is judged that the BMI is (○) but that the body fat ratio and the abdomen visceral fat sectional area are both (X), it is judged that the possibility of the disease such as diabetes and obesity is higher by the fact that the body fat mass and, further, the abdomen visceral fat mass are great, although it is judged that body type is good.

Also, for example, in case of the human subject 1 shown in FIG. 7, it is judged that the BMI and the body fat ratio are ○ and the visceral fat sectional area is X. In this case, it is judged that there is a possibility of disease because fat is concentratively deposited in the vicinity of visceral organs although body type and body fat mass are in a moderate range.

Industrial Availability

As described above, the health condition judgment display device according to the present invention is capable of making total judgment of health condition based on a plurality of indices relating to health condition. In addition, the device is capable of objectively making judgment of the risk of developing disease according to relationship between disease and a plurality of indices considered as factors of the disease.

What is claimed is:

1. A health condition judgment display device comprising:
   an input means with which individual body characteristic information of a body of a human subject is input;
   a measuring means for measuring body measurement information obtained by measurement made for the body of the human subject;
   a data processing portion capable of storing body information including the individual body characteristic information of the body input with the input means and the body measurement information measured by the measuring means and obtaining an index relating to health condition of the body of the human subject by data processing based on the stored body information; and
   a display means capable of displaying the body information including the individual body characteristic information and the body measurement information and the obtained index relating to health condition, wherein
   at least two indices relating to health condition are obtained,
   the measuring means includes a body impedance measuring means capable of measuring body impedance of the entire body and/or each portion of the body,
   the body measurement information includes the body impedance of each portion of the body and/or the entire body,
   the individual body characteristic information includes body height, body weight, age, and sex,
   the body information includes information of body fat mass, body fat ratio, fat-free mass, body water mass, and muscle mass of each of the body and/or the entire body, which are obtained based on the body height, the body weight, the age, the sex, and the body impedance of each portion of the body and/or the entire body,
   the body information includes waist size, hip size, subcutaneous fat thickness, abdomen visceral fat sectional area, abdomen subcutaneous fat sectional area, and thigh muscle sectional area,
   the indices relating to health condition further include a body mass index (BMI), a ratio of the waist size to the hip size (W/H ratio), a ratio of the visceral fat to the subcutaneous fat (V/S ratio), a ratio of the body fat mass to the body water mass, a ratio of the body water mass to the body weight, and a ratio of the body fat ratio to leg muscle mass, and
   the indices relating to health condition further include abdomen visceral fat sectional area, waist size, and odds ratio.

2. A health condition judgment display device comprising:
   an input means with which individual body characteristic information of a body of a human subject is input;
   a measuring means for measuring body measurement information obtained by measurement made for the body of the human subject;
   a data processing portion capable of storing body information including the individual body characteristic information of the body input with the input means and the body measurement information measured by the measuring means and obtaining an index relating to health condition of the body of the human subject by data processing based on the stored body information; and
   a display means capable of displaying the body information including the individual body characteristic information and the body measurement information and the obtained index relating to health condition, wherein
   at least two indices relating to health condition are obtained,
   the measuring means includes a body impedance measuring means capable of measuring body impedance of the entire body and/or each portion of the body,
   the body measurement information includes body impedance of each portion of the body and/or the entire body,
   the individual body characteristic information includes body height, body weight, age, and sex,
   the body information includes information of body fat mass, body fat ratio, fat-free mass, body water mass, and muscle mass of each portion of the body and/or the entire body, which are obtained based on the body height, the body weight, the age, the sex, and the body impedance of each portion of the body and/or the entire body,
   the body information includes waist size and hip size of the human subject, and the indices relating to health condition include a body mass index (BMI), body fat ratio, abdomen visceral fat sectional area, and waist size.

3. A health condition judgment display device comprising:
- an input means with which individual body characteristic information of a body of a human subject is input;
- a measuring means for measuring body measurement information obtained by measurement made for the body of the human subject;
- a data processing portion capable of storing body information including the individual body characteristic information of body input with the input means and body measurement information measured by the measuring means and obtaining an index relating to health condition of the body of the human subject by data processing based on the stored body information; and
- a display means capable of displaying the body information including the individual body characteristic information and the body measurement information and the obtained index relating to health condition, wherein
  - at least two indices relating to health condition are obtained, and
  - the measuring means includes a body impedance measuring means capable of measuring body impedance of the entire body and/or each portion of the body,
  - the body measurement information includes body impedance of each portion of the body and/or the entire body,
  - the individual body characteristic information includes body height, body weight, age, and sex,
  - the body information includes body fat mass, body fat ratio, fat-free mass, body water mass, and muscle mass of each portion of the body and/or the entire body, which are obtained based on the body height, the body weight, the age, the sex, and the body impedance of each portion of the body and/or the entire body,
  - the body information includes waist size and hip size of the human subject, subcutaneous fat thickness, abdomen visceral fat sectional area, abdomen subcutaneous fat sectional area, and thigh muscle sectional area, and
  - the indices relating to health condition include a body mass index (BMI), body fat ratio, abdomen visceral fat sectional area, and waist size.

4. A health condition judgment display device comprising:
- an input means with which individual body characteristic information of a body of a human subject is input;
- a measuring means for measuring body measurement information obtained by measurement made for body of the human subject;
- a data processing portion capable of storing body information including the individual body characteristic information of the body input with the input means and the body measurement information measured by the measuring means and obtaining an index relating to health condition of the body of the human subject by data processing based on the stored body information; and
- a display means capable of displaying the body information including the individual body characteristic information and the body measurement information and the obtained index relating to health condition, wherein
  - at least two indices relating to health condition are obtained,
  - the measuring means includes a body impedance measuring means capable of measuring body impedance of the entire body and/or each portion of the body,
  - the body measurement information includes body impedance of each portion of the body and/or the entire body,
  - the individual body characteristic information includes body height, body weight, age, and sex,
  - the body information includes information of body fat mass, body fat ratio, fat-free mass, body water mass, and muscle mass of each portion of the body and/or the entire body, which are obtained based on the body height, the body weight, the age, the sex, and the body impedance of each portion of the body and/or the entire body,
  - the indices relating to health condition include a ratio of the body fat mass to the muscle mass (F/M ratio) for the entire body and each portion of the body, and
  - the indices relating to health condition further include a body mass index (BMI), body fat ratio, abdomen visceral fat sectional area, and waist size.

5. A health condition judgment display device comprising:
- an input means with which individual body characteristic information of a body of a human subject is input;
- a measuring means for measuring body measurement information obtained by measurement made for the body of the human subject;
- a data processing portion capable of storing body information including the individual body characteristic information of the body input with the input means and the body measurement information measured by the measuring means and obtaining an index relating to health condition of the body of the human subject by data processing based on the stored body information;
- a display means capable of displaying the body information including the individual body characteristic information and the body measurement information and the obtained index relating to health condition, wherein
  - at least two indices relating to health condition are obtained, and
  - the measuring means includes a body impedance measuring means capable of measuring body impedance of the entire body and/or each portion of the body,
  - the body measurement information includes body impedance of each portion of the body and/or the entire body,
  - the individual body characteristic information includes body height, body weight, age, and sex,
  - the body information includes information of body fat mass, body fat ratio, fat-free mass, body water mass, and muscle mass of each portion of the body and/or the entire body, which are obtained based on the body height, the body weight, the age, the sex, and the body impedance of each portion of the body and/or the entire body,
  - the body information includes waist size, hip size, subcutaneous fat thickness, abdomen visceral fat sectional area, abdomen subcutaneous fat sectional area, and thigh muscle sectional area,
  - the indices relating to health condition includes a ratio of the body fat mass to the muscle mass (F/M ratio) for the entire body and each portion of the body, and
  - the indices relating to health condition further include a body mass index (BMI), a ratio of the waist size to the hip size (W/H ratio), a ratio of the visceral fat to the subcutaneous fat (V/S ratio), a ratio of the body fat mass to the body water mass, a ratio of the body water mass to the body weight, and a ratio of the body fat ratio to leg muscle mass.

6. A health condition judgment display device comprising:
- an input means with which individual body characteristic information of a body of a human subject is input;
- a measuring means for measuring body measurement information obtained by measurement made for the body of the human subject;
- a data processing portion capable of storing body information including the individual body characteristic information of the body input with the input means and the body measurement information measured by the measuring means and obtaining an index relating to health condition of the body of the human subject by data processing based on the stored body information; and
- a display means capable of displaying the body information including the individual body characteristic information and the body measurement information and the obtained index relating to the health condition, wherein
  at least two indices relating to health condition are obtained, and
  the measuring means includes a body impedance measuring means capable of measuring body impedance of the entire body and/or each portion of the body,
  the body measurement information includes body impedance of each portion of the body and/or the entire body,
  the individual body characteristic information includes body height, body weight, age, and sex,
  the body information includes information of body fat mass, body fat ratio, fat-free mass, body water mass, and muscle mass, for each portion of the body and/or the entire body, which are obtained based on the body height, the body weight, the age, the sex, and the body impedance of each portion of the body and/or the entire body,
  the body information includes waist size, hip size, subcutaneous fat thickness, abdomen visceral fat sectional area, abdomen subcutaneous fat sectional area, and thigh muscle sectional area, and
  the indices relating to health condition include a ratio of the body fat mass to the muscle mass (F/M ratio) for the entire body and each portion of the body,
  the indices relating to health condition further include a body mass index (BMI), a ratio of the waist size to the hip size (W/H ratio), a ratio of the visceral fat to the subcutaneous fat (V/S ratio), a ratio of the body fat mass to the body water mass, a ratio of the body water mass to the body weight, and a ratio of the body fat ratio to leg muscle mass, and
  the indices relating to health condition further include abdomen visceral fat sectional area, waist size, and odds ratio.

7. The health condition judgment display device according to any of claims 1–6, wherein the indices relating to health condition include ratios relating to balance of the body impedance, the body water mass, and the muscle mass, between left half of the body and right half of the body.

8. The health condition judgment display device according to any of claims 1–6, wherein the indices relating to health condition include ratios relating to balance of the body impedance, the body water mass, and the muscle mass, between upper half of the body and lower half of the body.

9. The health condition judgment display device according to any of claims 1–6, wherein information of various types of diseases are stored, and
items of the indices relating to health condition as factors of each disease and their associated allowable values are stored for each of the diseases, further comprising:
  a comparing means that compares each of the indices relating to health condition to the allowable value.

10. The health condition judgment display device according to any of claims 1–6, wherein information of various types of diseases are stored, and
items of the indices relating to health condition as factors of each disease and their associated allowable values are stored for each of the diseases, further comprising:
  a comparing means that compares each of the indices relating to health condition to the allowable value, wherein
    each of the indices is classified into two or more stages based on comparison made by the comparing means.

11. The health condition judgment display device according to any of claims 1–6, wherein information of various types of diseases are stored, and
items of the indices relating to health condition as factors of each disease and their associated allowable values are stored for each of the diseases, further comprising:
  a comparing means that compares each of the indices relating to health condition to the allowable value, wherein
    each of the indices is classified into two or more stages based on comparison made by the comparing means, and
    a combination of two or more indices is obtained according to the stages of each of the indices relating to health, and total judgment of health condition of the human subject is made according to the combination of the indices.

12. The health condition judgment display device according to any of claims 1–6, wherein information of various types of diseases are stored, and
items of the indices relating to health condition as factors of each disease and their associated allowable values are stored for each of the disease, further comprising:
  a comparing means that compares each of the indices relating to health condition to the allowable value, wherein
    each of the indices is classified into two or more stages based on comparison made by the comparing means,
    a combination of two or more indices is obtained according to the stages of each of the indices relating to health, and total judgment of health condition of the human subject is made according to the combination of the indices, and
    the comparing means compares the indices relating to health condition to the allowable values by weighting according to type of the indices and according to type of disease.

13. The health condition judgment display device according to any of claims 1–6, wherein information of various types of diseases are stored, and
items of the indices relating to health condition as factors of each disease and their associated allowable values are stored for each of the diseases, further comprising:
  a comparing means that compares each of the indices relating to health condition to the allowable value, wherein
    the display means is adapted to select and display the items of the indices relating to health condition which are associated with each of the diseases and the obtained indices relating to health condition, corresponding to the respective items of the indices, for each of the diseases.

14. The health condition judgment display device according to any of claims 1–6, wherein information of various types of diseases are stored, and
items of the indices relating to health condition as factors of each disease and their associated allowable values are stored for each of the diseases, further comprising:
a comparing means that compares each of the indices relating to health condition to the allowable value, wherein
it is judged whether each of the indices relating to health condition is good or bad, according to comparison between each of the indices and the allowable value, and
the display means is adapted to arrange and display results of good or bad, for the respective judged indices relating to health condition.

15. The health condition judgment display device according to any of claims 1–6, wherein information of various types of diseases are stored, and
items of the indices relating to health condition as factors of each disease and their associated allowable values are stored for each of the diseases, further comprising:
a comparing means that compares each of the indices relating to health condition to the allowable value, wherein
it is judged whether each of the indices relating to health condition is good or bad, according to comparison between each of the indices and the allowable value,
the display means is adapted to arrange and display results of good or bad, for the respective judged indices to health condition, and
the results of good or bad are arranged according to degree of correlation with disease associated with the indices.

16. The health condition judgment display device according to any of claims 1–6, wherein information of various types of diseases are stored, and
items of the indices relating to health condition as factors of each disease and their associated allowable values are stored for each of the diseases, further comprising:
a comparing means that compares each of the indices relating to health condition to the allowable value, wherein
it is judged whether each of the indices relating to health condition is good or bad, according to comparison between each of the indices and the allowable value,
the display means is adapted to arrange and display results of good or bad, for the respective judged indices relating to health condition, and
the results of good or bad are arranged according to degree of correlation with disease associated with the indices,
to each of results of good and bad of a first index having correlation with disease, results of good and bad of a second index having correlation lower than that of the first index are connected, the results of good and bad of the first and second indices being hierarchically represented, and
an appropriate side corresponding to a judgment result for the human subject is selected and displayed, among the results of good and bad of the first and second indices.

17. The health condition judgment display device according to any of claims 1–6, wherein information of various types of diseases are stored, and
items of the indices relating to health condition as factors of each disease and their associated allowable values are stored for each of the diseases, further comprising:
a comparing means that compares each of the indices relating to health condition to the allowable value, wherein
it is judged whether each of the indices relating to health condition is good or bad, according to comparison between each of the indices and the allowable value,
the display means is adapted to arrange and display results of good or bad, for the respective judged indices relating to health condition, and
the results of good or bad are arranged according to degree of correlation with disease associated with the indices,
to each of results of good and bad of a first index having correlation with disease, results of good and bad of a second index having correlation lower than that of the first index are connected, the results of good and bad of the first and second indices being hierarchically represented,
an appropriate side corresponding to a judgment result for the human subject is selected and displayed, among the results of good and bad of the first and second indices, and
the indices for which judgment results are displayed include BMI, body fat ratio, and abdomen visceral fat sectional area.

18. The health condition judgment display device according to any of claims 1–6, wherein, information of various types of diseases are stored, and
items of the indices relating to health condition as factors of each disease and their associated allowable values are stored for each of the diseases, further comprising:
a comparing means that compares each of the indices relating to health condition to the allowable value, wherein
it is judged whether each of the indices relating to health condition is good or bad, according to comparison between each of the indices and the allowable value,
the display means is adapted to arrange and display results of good or bad, for the respective judged indices relating to health condition, and
the results of good or bad are selected and displayed for each of the diseases.

19. The health condition judgment display device according to any of claims 1–6, wherein, information of various types of diseases are stored, and
items of the indices relating to health condition as factors of each disease and their associated allowable values are stored for each of the diseases, further comprising:
a comparing means that compares each of the indices relating to health condition to the allowable value, wherein
the diseases include diabetes, dehydration, and metabolic defect.

20. The health condition judgment display device according to any of claims 1–6, the measuring means includes a body weight measuring means capable of measuring body weight of the human subject.

* * * * *